United States Patent [19]

Anderson et al.

[11] 4,440,177
[45] Apr. 3, 1984

[54] RESPIRATORY ANALYZER SYSTEM

[75] Inventors: Stephen T. Anderson; Catherine A. Anderson, both of Stillwater, Minn.

[73] Assignee: Medical Graphics Corporation, Shoreview, Minn.

[21] Appl. No.: 331,247

[22] Filed: Dec. 16, 1981

Related U.S. Application Data

[63] Continuation-in-part of Ser. No. 165,949, Jul. 3, 1980, abandoned.

[51] Int. Cl.³ ............................................. A61B 5/08
[52] U.S. Cl. .................................... 128/719; 128/725
[58] Field of Search .............................. 128/718–719, 128/721–722, 725, 203.22, 203.25, 204.22

[56] References Cited

U.S. PATENT DOCUMENTS

| | | | |
|---|---|---|---|
| 3,896,792 | 7/1975 | Vail et al. | 128/719 |
| 3,927,670 | 12/1975 | Turney et al. | 128/719 |
| 4,178,919 | 12/1979 | Hall | 128/719 |
| 4,221,130 | 9/1980 | Burrows | 128/719 X |
| 4,221,224 | 9/1980 | Clark | 128/718 |

OTHER PUBLICATIONS

Talbot, T. L. et al., "Breath by Breath Gas Analysis During Exercise Stress Testing", Conf. Adv. in Bioengineering New York, Dec. 2-7, 1979.

Primary Examiner—Kyle L. Howell
Assistant Examiner—Francis J. Jaworski
Attorney, Agent, or Firm—Orrin M. Haugen; Thomas J. Nikolai

[57] ABSTRACT

A system for measuring the ventilatory response of the human respiratory system to increased levels of $CO_2$ and/or decreased levels of $O_2$. Measured concentrations of $CO_2$ are introduced into an infant's lungs and the inspired and expired air is passed through a pneumotachograph for developing various electrical analog signals relating to flow. Samples of the expired air are delivered to $CO_2$ and $O_2$ analyzers. The resulting electrical analog signals produced by these devices represent inspiratory and expiratory flow, and the $CO_2$ and the $O_2$ levels in the expired air. They are applied to a waveform analyzer containing an analog to digital converter and a microprocessor system which is programmed to discriminate between normal breathing patterns and irregular patterns. The microprocessor also computes inspiratory and expiratory tidal volume, ventilation (measured in liters per minute), breathing frequency, inspiratory, expiratory and total times of a preceding breath, minimum $CO_2$ and $O_2$, peak $CO_2$ and $O_2$ and volume of expired $CO_2$ and $O_2$ either on a breath-by-breath basis or over a user selected time interval. The results of these computations are provided in digital form to a digital computer having a graphic display capability. When the ventilation rate is plotted as a function of changes in the inspired $CO_2$ concentration, the slope of this linear relation is indicative of abnormal ventilatory response, which is deemed helpful in the diagnosis of a number of disease states, e.g., Sudden Infant Death Syndrome.

7 Claims, 14 Drawing Figures

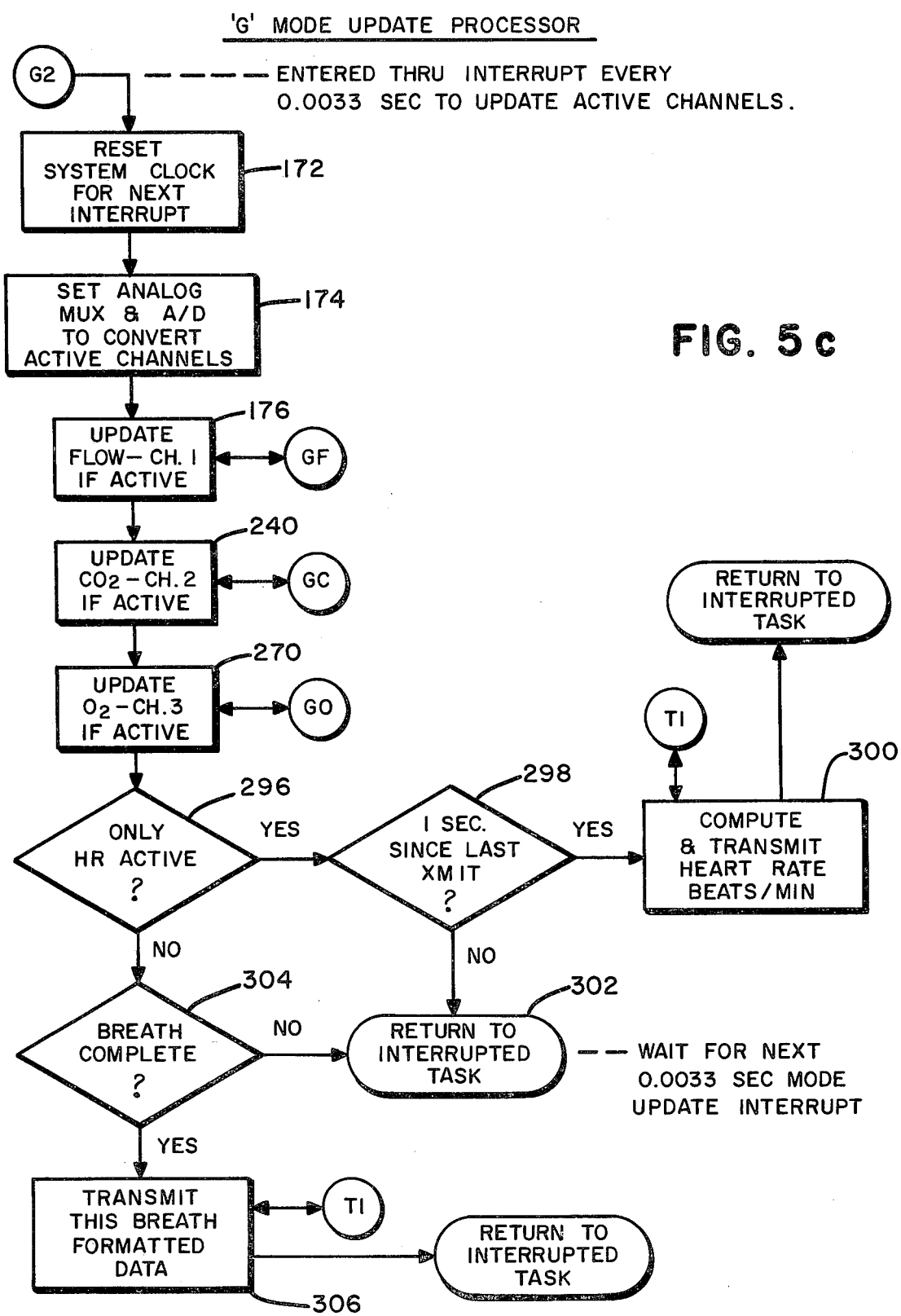

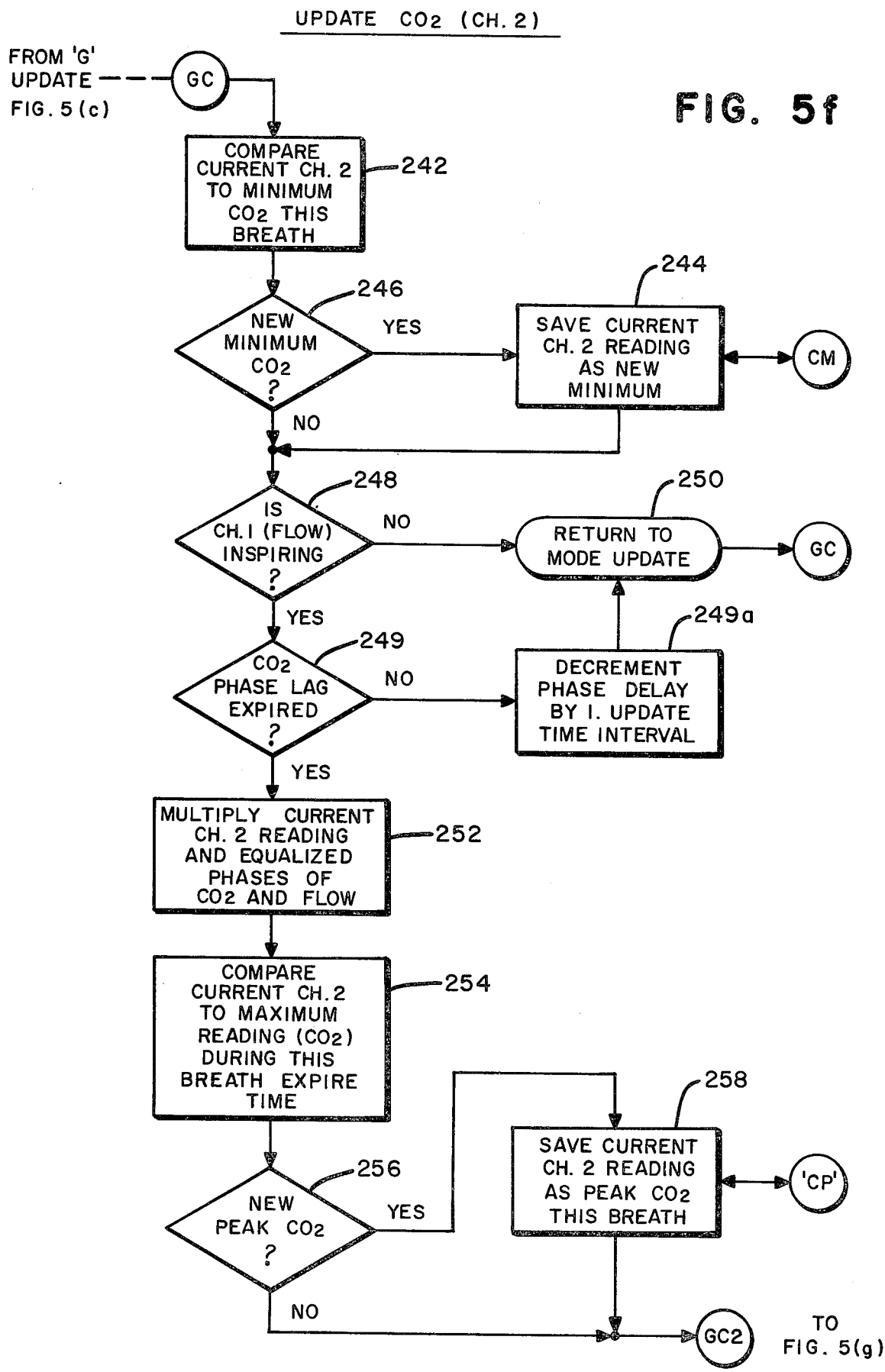

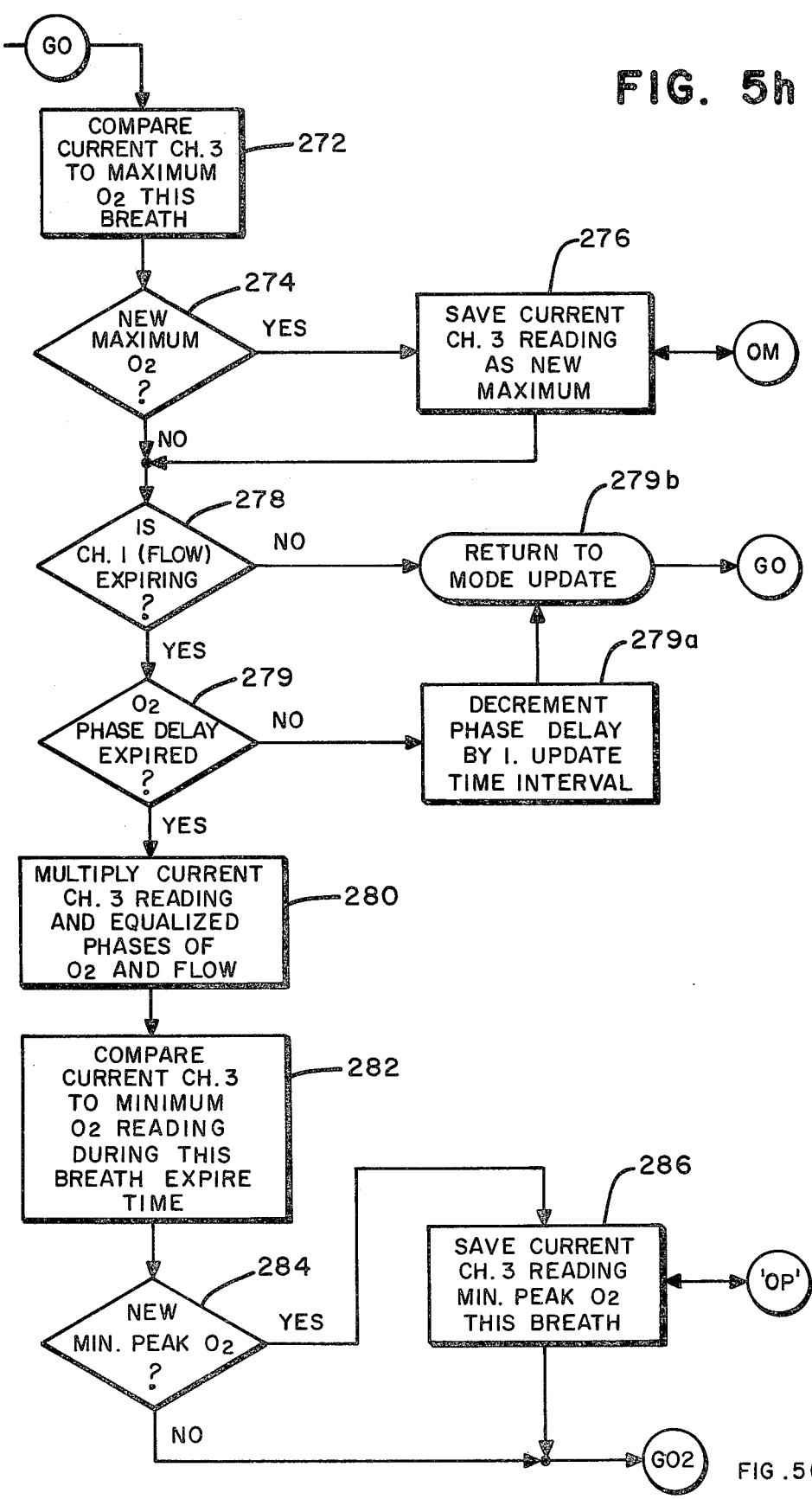

RESPIRATORY ANALYZER SYSTEM

CROSS-REFERENCE TO RELATED APPLICATION

This is a continuation-in-part of application Ser. No. 165,949 filed July 3, 1980 (now abandoned).

BACKGROUND OF THE INVENTION

I. Field of the Invention:

This invention relates generally to an electronic medical instrumentation system and more specifically to a real time data processing and display system whereby respiratory system impairments can be determined.

II. Discussion of the Prior Art:

In a paper entitled "Abnormal Regulation of Ventilation in Infants at Risk for Sudden-Infant-Death Syndrome" by Daniel C. Shannon et al, published in the Oct. 6, 1977 issue of The New England Journal of Medicine, Volume 297, No. 14 at pp 747–50, there is described a method for determining the sensitivity of the infant's respiratory response to variations in concentrations of inspired $CO_2$. In normal infants, an increase in inspired $CO_2$ results in an increase in the ventilation. However, with infants who are subject to chronic sleep hypoventilation or periods of prolonged apnea during sleep, it was found that there was a significant reduction in the change in ventilation per change in partial pressure of carbon dioxide in the inspired breath. Those infants that had a history of prolonged sleep apnea episodes exhibited a change in minute ventilation in response to carbon dioxide breathing which was significantly less than that in the control group of infants. This difference was attributed primarily to a significantly smaller increase in tidal volume, which accounts for most of the ventilatory response in normal infants. Dr. Shannon and his co-workers concluded, based upon studies conducted, that impaired regulation of alveolar ventilation is an explanation for sleep apnea.

The ability of the respiratory system to react to changes in gas concentration can be measured and the sensitivity of the respiratory system noted. Results of such tests have produced useful information, and demonstrated variances in sensitivity according to the maturity of the respiratory system. The ventilatory response to decreased levels of oxygen in adults is far less than that measured in neonates. Neonates will show a measurable increase in breathing rate when they inspire a mixture of 18% $O_2$ rather than the normal 21%. The normal respiratory response to inspired $CO_2$ is an increase in ventilation for an increase in alveolar or arterial $CO_2$ concentration. The slope of the derived curve of ventilation versus $CO_2$ concentration may then be used as an index of how sensitive the respiratory system is to changes in $CO_2$ concentration.

Ventilatory response measurements, when taken on pre-term infants, tend to show a flatter slope, $$\frac{\dot{V}_E \text{ final} - V_E \text{ initial}}{PACO_2 \text{ final} - PACO_2 \text{ initial}}$$

where $\dot{V}_E$ initial is the ventilation at normal inspired $CO_2$ levels and $V_E$ final is the ventilation at an increased $CO_2$ level. $PACO_2$ initial and $PACO_2$ final refer to the partial pressure of the alveolar or end tidal $CO_2$ at normal and increased inspired $CO_2$ levels, respectively. The decrease has been shown to be directly related to the maturity of the central nervous system (CNS). Hence, by measuring the slope of normal ventilation versus levels of $CO_2$ while maintaining the inspired oxygen concentration constant at 21%, one is able to determine the relative maturity of the respiratory system. Where a lower than normal slope is exhibited, a physician will be better able to inform the parents as to the risk of SIDS. With such information, the parents may be relieved of unnecessary worry or, alternatively, they will be instructed such that they can have the infant monitored and medically treated during the immature state. The respiratory maturity typically occurs within the first few months but may not occur for a period of 24 months in a small population of infants at risk.

Systems to measure metabolic rate or physiological changes due to exercise stress are somewhat related to the present invention. A system of this type is described in the Rummel et al U.S. Pat. No. 3,799,149 and includes apparatus for measuring $CO_2$ and $O_2$ in inspired and expired breath as well as changes in ventilation. The apparatus described in the Rummel et al patent, while perhaps satisfactory for adult subjects, is totally unsatisfactory for use with infants. For the system of the Rummel et al patent to operate satisfactory, the sample size necessary for measurement of the gases is too large to be used with infants and drastically affects the ventilation as well as gas concentration data. Because infants are more sensitive to the introduction of sampling devices into the mouth or nasal passages than are adults, it is difficult to obtain accurate data when it is noted that consistent breathing patterns tend only to be available when the infant is in a "deep sleep" state as distinguished from REM (rapid eye movement) sleep. Unless a deep sleep condition can be reached, the data obtained from systems of the prior art are subject to error. Anything which interferes with the ability to achieve the deep sleep state, such as the presence of an uncomfortable object in the patient's nose, is therefore to be avoided.

SUMMARY OF THE INVENTION

In accordance with the techings of the present invention, there is provided a system for monitoring and continuously measuring the ventilatory response of patients, primarily neonates, to changes in $CO_2$ concentrations in inspired air. The system includes a specially designed nosepiece with a pneumotach which may be comfortably attached to the nasal openings of the patient and held in place by a means which does not tend to cause irritation or fussiness. Further, the nosepiece is designed to preclude expired gases from leaking past the outer surfaces of the tubular nasal inserts to the atmosphere, but instead, the total volume of inspired and expired air is made available to the test apparatus. The pneumotach is, in turn, coupled through suitable tubing to a capacitance-type differential pressure transducer used to convert alternating differential pressures obtained from it into electrical signals. The alternating differential pressures are, of course, created within the pneumotach attached to the nosepiece by the breathing of the subject, negative pressures being developed during inspiration and positive pressures during expiration. The electrical signals obtained from the pneumotach and pressure transducer are amplified and applied as a first input to a waveform analyzer.

Provision is made for introducing measured concentrations of various gases, including $O_2$ and $CO_2$ through the nosepiece into the patient's respiratory system. The system further includes means for sampling the patient's expired air and the sample is delivered to a $CO_2$ analyzer and an $O_2$ analyzer, these analyzers also providing separate inputs to the aforementioned waveform analyzer. The waveform analyzer functions to eliminate abnormal data which may occur during the test period. Specifically, those variations occurring during REM sleep tend to be quite irregular in frequency and amplitude from the pattern obtained when the subject is in deep sleep and, if not properly filtered out from the sampled data, could lead to erroneous results. However, these irregular breathing patterns are retained in the computer storage and can be used to determined apneic durations.

The waveform analyzer of the present invention is a microprocessor-based device which allows it to perform computations based on the inputs received on a breath-by-breath basis. It also includes circuitry for converting the analog signals into a digital format prior to processing and following these computations, the digital output from the waveform analyzer is, in turn, coupled to an auxiliary computing device controlling a printer/plotter. Because the manner in which the waveform analyzer and the computer are programmed, the printer/plotter is made to generate, on a breath-by-breath (real-time) basis, a plot of ventilation, measured in milliliters per minute per kilogram of body weight, as a function of end-tidal partial pressure of carbon dioxide, measured in millimeters of mercury. By noting the slope of the curve and comparing that slope with data obtained from normal subjects i.e., those not suffering from respiratory dysfunction, a judgement can be made as to any respiratory impairment (specifically, brain stem impairment) and in the case of infants, their propensity towards disease states such as SIDS. The slope of the aforementioned curve for normal infants tends to be significantly steeper than that obtained from infants who have had one or more episodes of sleep apnea. In this fashion, a judgement may be made by an attending physcian as to the need for sleep monitoring apparatus or other applicable treatment procedures.

OBJECTS

It is accordingly the principal object of the present invention to provide a new and improved system for measuring respiratory response of patients to changes in $CO_2$ concentration in inspired air.

Another object of the invention is to provide a system of the type described which is compatible with neonates.

A still further object of the invention is to provide an apparatus for computing on a breath-by-breath basis, in real time, the ventilation occurring for given values of partial pressure of $CO_2$ in the inspired air.

A still further object of the invention is to provide a system, especially designed for use with neonates, for measuring and plotting curves whose slopes are indicative of the change in ventilation for a given change in inspired levels of $CO_2$, the data being obtained and displayed on a real time basis from such neonates during deep sleep states.

A still further object of the present invention is to provide a system of the type described in which irregular breath samples are effectively removed from the computation process, thereby improving the accuracy of the measurements obtained by the system.

These and other objects and advantages of the invention will become apparent to those skilled in the art from the following detailed description of a preferred embodiment, when considered in conjunction with the accompanying drawings.

DESCRIPTION OF THE DRAWINGS

FIGS. 5(a) through 5(i) are flow charts showing a preferred way of programming the microprocessor based waveform analyzer; and FIG. 6 illustrates typical plots prepared by the printer/plotter device of FIG. 2.

DESCRIPTION OF THE PREFERRED EMBODIMENT

Figure 1:
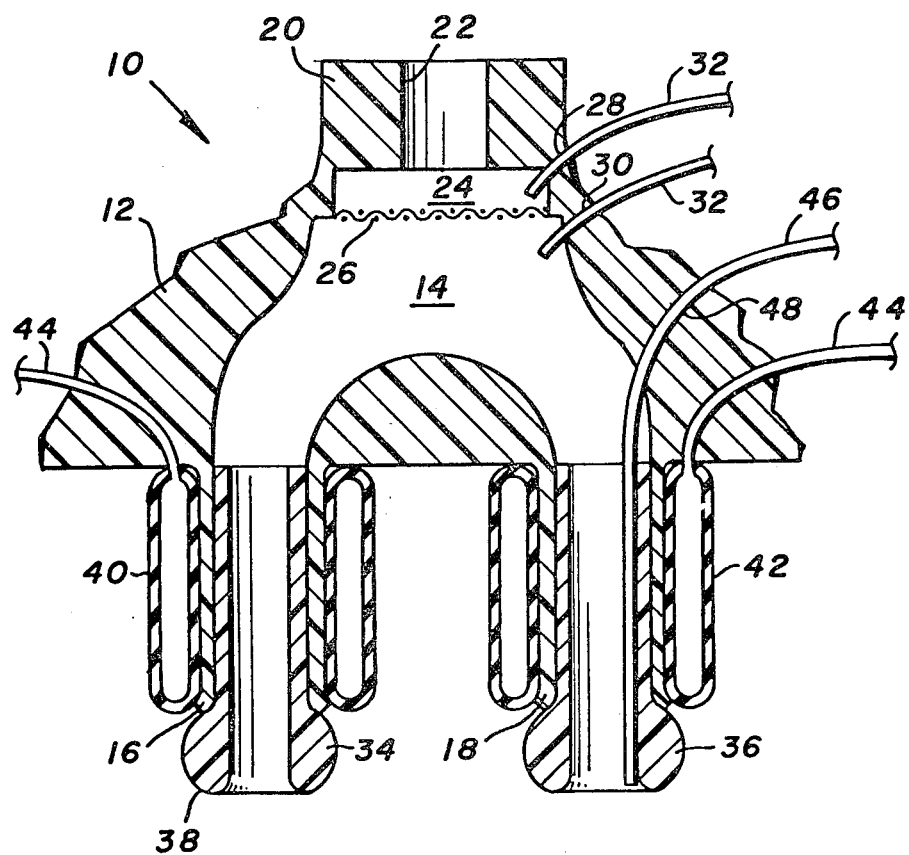
FIG. 1 is a cross-sectional view of one possible nosepiece which may be used in the system, included for example and for the purpose of illustration only.

Before describing the overall system of the present invention, attention is first directed to the mechanical construction of a nosepiece which has been especially designed to allow precise, accurate measurements of respiratory flow and allowing for the introduction of measured concentrations of gases and the sampling of expired gases from the subject's respiratory system. As can be seen from FIG. 1, the nosepiece 10 comprises a body member 12 which is preferably formed from a soft, flexible rubber-like material having a cavity as at 14 formed therein and having tubular projections 16 and 18 extending outwardly from the body, the lumens of these tubular projections communicating with the cavity 14. The body member 12 further includes an oppositely directed stem portion 20 having a bore 22 extending inwardly toward the cavity 14 and terminating in cylindrical enlargement 24. A screen member 26 is disposed between the enlargement 24 and the cavity 14 and small ports as at 28 and 30 are formed through the material of the body member 12 to allow lengths of flexible plastic tubing 32 to be introduced therethrough, the ports 28 and 30 being disposed on opposite sides of the screen member 26.

First and second insert members 34 and 36 are provided and comprise generally tubular structures having a bulbous terminal portion as at 38, these members being formed from a generally rigid plastic material and being generally cylindrical over the remaining portion of their lengths so as to be insertable into the lumen of the tubular projections 16 and 18.

Surrounding the tubular projections 16 and 18 are first and second expander members 40 and 42 which are preferably adhesively bonded in place on the tubular projections of the body member 12. These expander members are preferably formed from a flexible, inelastic material and are toroidally shaped. Each of the expander members includes a port into which is fitted a length of tubing as at 44 which permits air under pressure to be introduced into the expanders causing them to be inflated.

Further included in the nosepiece of FIG. 1 is a tube element 46 which may be introduced through a bore 48 formed through the body member 12 and extending through the cavity 14 and into the central opening of the reinforcing member 36. By connecting the tube element 46 to a suitable gas supply, controlled amounts of predetermined gases may be introduced into the subject's respiratory system.

In use, the nosepiece of FIG. 1 is inserted into the patient's nasal openings and air is introduced through the tube elements 44 so as to inflate the expander members 40 and 42. Once expanded, air is precluded from leaking between the side walls of the nasal passages and the exterior mating surfaces of the nosepiece.

The screen 26 is perferably a 400 mesh Monel screen, a type that is commonly found in Fleisch-type pneumotachs. By controlling the size of the bore 22 and the extension 24 thereof, only a small dead space is involved, thereby precluding the subject from breating his own expired $CO_2$. The tubular elements 32 are adapted to be connected to the Pressure Transducer itself for monitoring pressure differentials across the screen 26. While not shown in FIG. 1, it is also possible to incorporate electrical heater elements within the cavity 14 for the purpose of eliminating the formation of condensation within the cavity.

Figure 2:
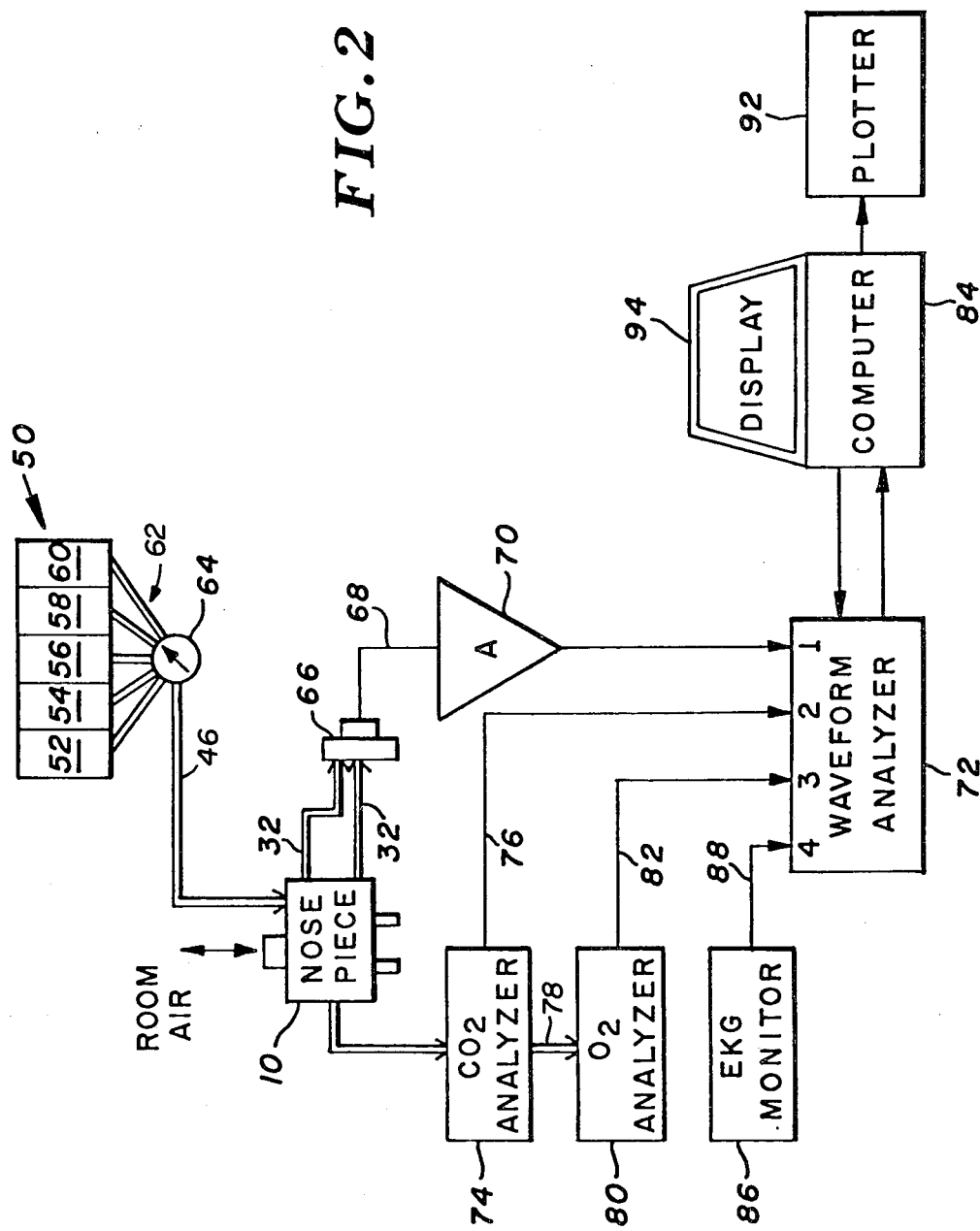
FIG. 2 is a general block diagram illustrating the preferred embodiment.

With reference to FIG. 2, the system of the preferred embodiment which is designed to enable accurate measurement of ventilatory response to hypercapnia and hypoxia will be described. Numeral 50 indicates generally a gas flow metering device which includes a plurality of sealed chambers 52 through 60, each of which is arranged to contain a predetermined gas mixture. For example, chamber 52 may include compressed air, while chambers 54, 56, and 58 may, for example, contain 2%, 4%, and 6% carbon dioxide with the balance being air. Chamber 60 may be used to store pure nitrogen. A greater number of chambers may be included in the gas sample metering apparatus 50 to accommodate a greater number of concentrations. Alternatively, instead of having differing $CO_2$ concentrations stored in individual containers as illustrated, it is also possible to create the desired mixtures by combining $CO_2$ gas with room air in a single chamber under control of suitable measuring instrumentation to ensure that desired concentration is obtained. With respect to the apparatus illustrated, each of the chambers is adapted to be connected by suitable tubing, indicated generally by numeral 62, and a rotary selector valve 64 to the tube 46 entering the nosepiece of FIG. 1. As mentioned, the nosepiece of FIG. 1 includes a pneumo-mechanical flow head which, when attached to a pressure transducer, operates to convert gas flow into a differential pressure reading, the head being arranged for use in both open and closed-circuit respiratory gas systems. It is arranged to maintain a differential pressure measured between two points on opposite sides of the screen 26, this differential pressure being directly proportional to the gas flow.

The outputs from each side of the screen portion of the nosepiece are applied through tubes 32 to a capacitance-type pressure transducer member 66 which may be considered as a part of the pneumotachograph. The pressure transducer 66 functions to convert the alternating differential pressures obtained during inspiration and expiration of breath through the nosepiece 10 to electrical signals which are directly proportional to the respiratory gas flow. The electrical signals are, in turn, applied by way of a conductor 68 to the input of an amplifier 70 and from there to a first input channel of a waveform analyzer 72.

The sample tube 20 is adapted to be connected to the input of a $CO_2$ Analyzer 74. The analyzer 74 is preferably of the type designed to measure the concentration of carbon dioxide in an expiratory gas mixture by utilizing infrared absorption techniques. It should be understood, however, that other devices are available for measuring $CO_2$ partial pressures in a gas mixture and, hence, the invention is not limited to the use of the infrared absorption type. The output from the analyzer 74 is an electrical analog waveform corresponding to real time $CO_2$ concentration during the monitored respiratory cycles. This electrical signal appears on conductor 76 and is also applied as an input to a separate channel of the waveform analyzer 72.

The sampled expiratory gas mixture passes through the analyzer 74 and through the tube 78 to the inlet port of an $O_2$ analyzer 80 which, too, provides an electrical output that is a measure of the partial pressure of oxygen in the gas mixture being sampled. This electrical signal on line 82 is applied to a third input channel of the waveform analyzer 72. By including an $O_2$ analyzer and by including a sample of pure nitrogen in chamber 60, the system may be used for measuring the respiratory response to both hypercapnia and hypoxia.

As will be more fully set forth hereinbelow, the waveform analyzer 72 is preferably a microprocessor based instrument designed to analyze analog waveforms and programmed to compare received waveforms with a predetermined standards such that those waves not conforming to the standard will be eliminated from further processing operations. In this connection, the waveform analyzer may be capable of measuring and storing values corresponding to the peaks of a received waveform and the frequency of the incoming signals. Provision is also made in the waveform analyzer to allow it to be under control of an external device, such as the general purpose digital computer as at 84, the waveform analyzer 72 being provided with a serial interface configuration which may include, for example, a RS-232-C or 20 Ma current loop. By including a microprocessor type control in the waveform analyzer, it is possible to program the unit whereby a variety of inputs may be analyzed and specific tasks performed on the data in a desired sequence.

As indicated, there are four analog signal waveforms brought in on channels 1, 2, 3 and 4 of the waveform analyzer and they are respectively proportional to inspiratory flow, carbon dioxide and oxygen levels in the expiratory gas mixture and heart rate. The heart rate signal is conveniently obtained from an EKG type sensor 86 and is applied to channel 4 of the waveform analyzer by a conductor 88. Based upon these input signals, the waveform analyzer is arranged to process the received data to yield such parameters as tidal volume, ventilation (volume averaged over user selected time interval in ml/min) inspiratory time of last breath, pause time between inspiration and expiration, the total time of the preceding breath, breath frequency, etc. Utilizing the analog waveform from the carbon dioxide analyzer, the waveform analyzer may be programmed to compute the $CO_2$ peak value of a preceding breath and the volume of $CO_2$ of the preceding breath. Likewise, the analog signal obtained from the oxygen analyzer 56 may be processed within the waveform analyzer 72 to yield values indicative of the peak $O_2$ level of a preceding breath and the volume of $O_2$ of such preceding breath. The heart rate signal applied to channel 4 of the waveform analyzer is merely the heart rate measured in beats per minute.

The serial digital data from the waveform analyzer 72 may be applied through a serial interface to the computer 84 which is programmed to perform various computations on the received data. The computer may, for example, compute for each breath sample the ventilation value $V_E$ in liters per minute per kilogram of body weight and present the computed result to a printer/plotter 92. In addition, the computer 84 may be programmed to provide an instantaneous display read-out on the display screen 94 of a series of text-type instructions to the medical technologist so that the system will be properly calibrated and used. That is, the display 94 may present a sequential indication of the steps to be followed in performing the initial calibrations and the later patient testing functions. As such, the computer and display capability makes the system inter-active, thereby lessening the need for highly trained operating personnel.

Figure 3:
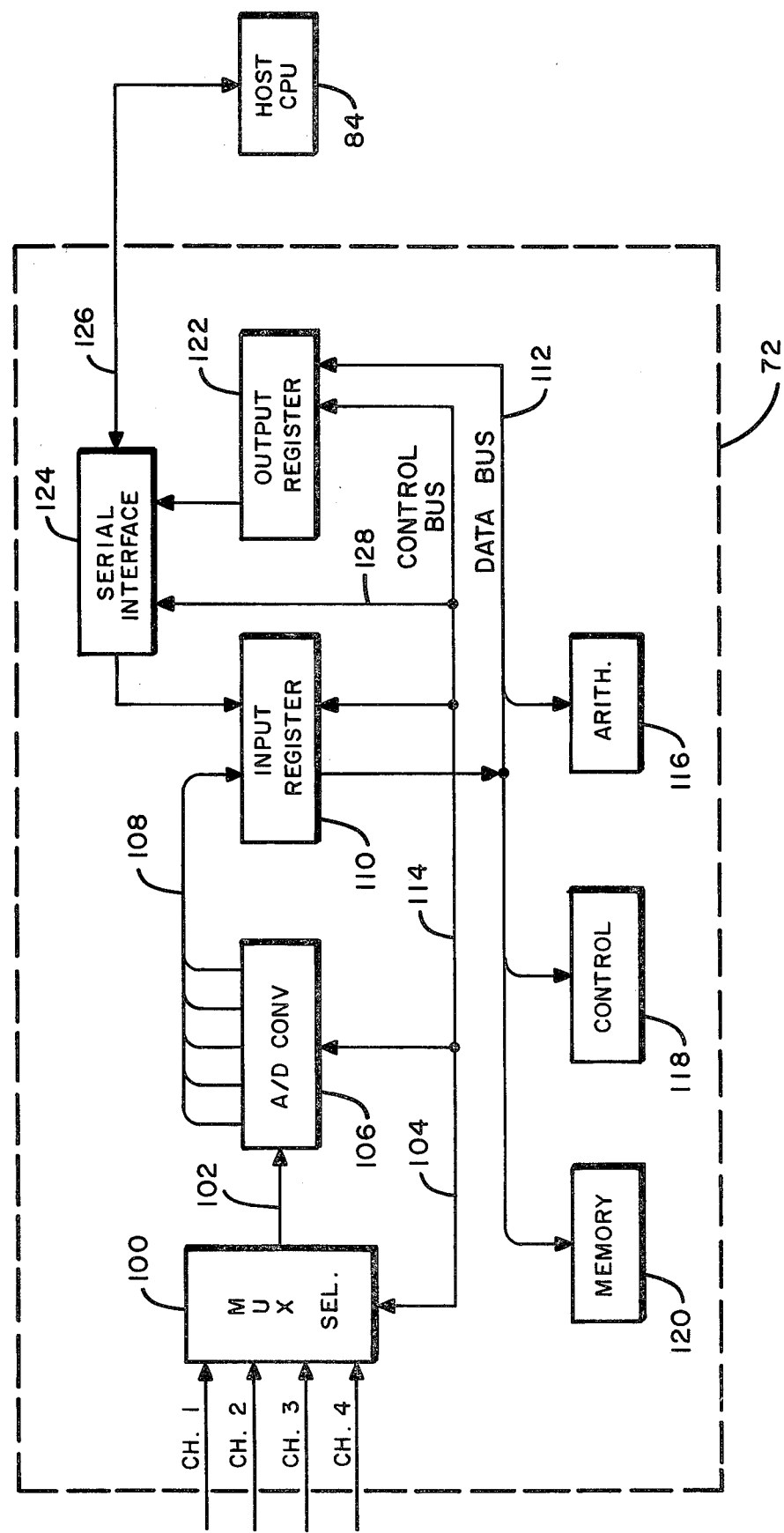
FIG. 3 is a block diagram of the waveform analyzer used in the system of FIG. 2.

Referring next to FIG. 3, there is shown by means of a block diagram the structural organization of the waveform analyzer 72 of FIG. 2. As is illustrated, the waveform analyzer includes an input multiplexer 100 having a plurality of input channels, e.g., CH.1—CH.4, to which the flow measuring apparatus and the gas analyzer apparatus and EKG monitor may be connected. The multiplexer functions in a conventional fashion to individually couple any one of the channels at a time to its output line 102 depending upon the signals applied to the selector inputs 104 of the multiplexer. The output line 102 is coupled to an input of an analog-to-digital converter 106 which operates in a known fashion to generate a binary code pattern on the output lines 108 which are indicative of the analog signal applied at its input.

The output from the A/D converter 106 is coupled to an input resister 110 of a bus structured microprocessor. Such a microprocessor includes a data bus 112 and a control bus 114 along with an arithmetic module 116, a control module 118 and a memory module 120. Each of the modules is adapted to receive control signals via the control bus 114 and to transmit or receive operand information via the data bus 112. As such, information from the input register 110 may be transferred via the data bus to the memory under control of the control module 118. Alternatively, data may be transferred between the memory module 120 and the arithmetic module 116 via the data bus 112.

Data from the memory 120, the arithmetic unit 116 or the control module 118 may also be transferred via the data bus 112 to an output register 122. Where a serial data transmission is desired, the output register 122 may have its individual stages applied to a parallel to serial converter (not shown) contained in the serial interface 124 and the serial output therefrom developed on line 126 may be clocked out at a rate determined by control signals applied via the control bus to the serial interface clock input 128. The data from the waveform analyzer 72 may be fed to the host computer 84 which is used to control a CRT display or a hard copy printer/plotter device as indicated in FIG. 2.

OPERATION

Now that the apparatus has been described, the operation of the system hardware will be more particularly set forth and in this regard, reference will be made to the waveforms of FIG. 4.

The patient whose respiratory response is to be measured has the nosepiece 10 inserted into the nostrils and the expander members 40 and 42 are inflated in such a fashion that no passage of air is permitted, except through the interior structures of the nosepiece. Following various calibration steps wherein the pneumotachograph 66, $CO_2$ analyzer 74 and the $O_2$ analyzer 80 are adjusted in accordance with instructions which are made to appear on the CRT display screen 94, air mixtures with predetermined differing concentrations of $CO_2$ gas, are sequentially introduced, via the metering arrangement 50 and the selector valve 64, into the nosepiece 10 during successive inspiratory cycles. The mixtures, one at a time, at spaced intervals are drawn through the pneumotachograph transducer head contained in the nosepiece and into the patient's lungs. During expiration, the flow direction through the pneumotachograph transducing head is reversed and, at approximately the same time, the $CO_2$ and the $O_2$ content of the expired gas mixture is determined by the analyzers 74 and 80, respectively, with electrical analog signals proportional to the partial pressure of each being applied to the waveform analyzer 72. The output from the transducing head also is coupled through sample tubes 32 to the pressure to electrical signal transducer 66 such that the resulting electrical signal on line 68 is proportional to inspiratory flow. This signal is also amplified at 70 and applied as an input to the waveform analyzer 72. Heart rate, measured in beats per minute, may conveniently be obtained from an EKG monitor 86 and applied, along with the other mentioned signals, to the waveform analyzer.

Figure 4:
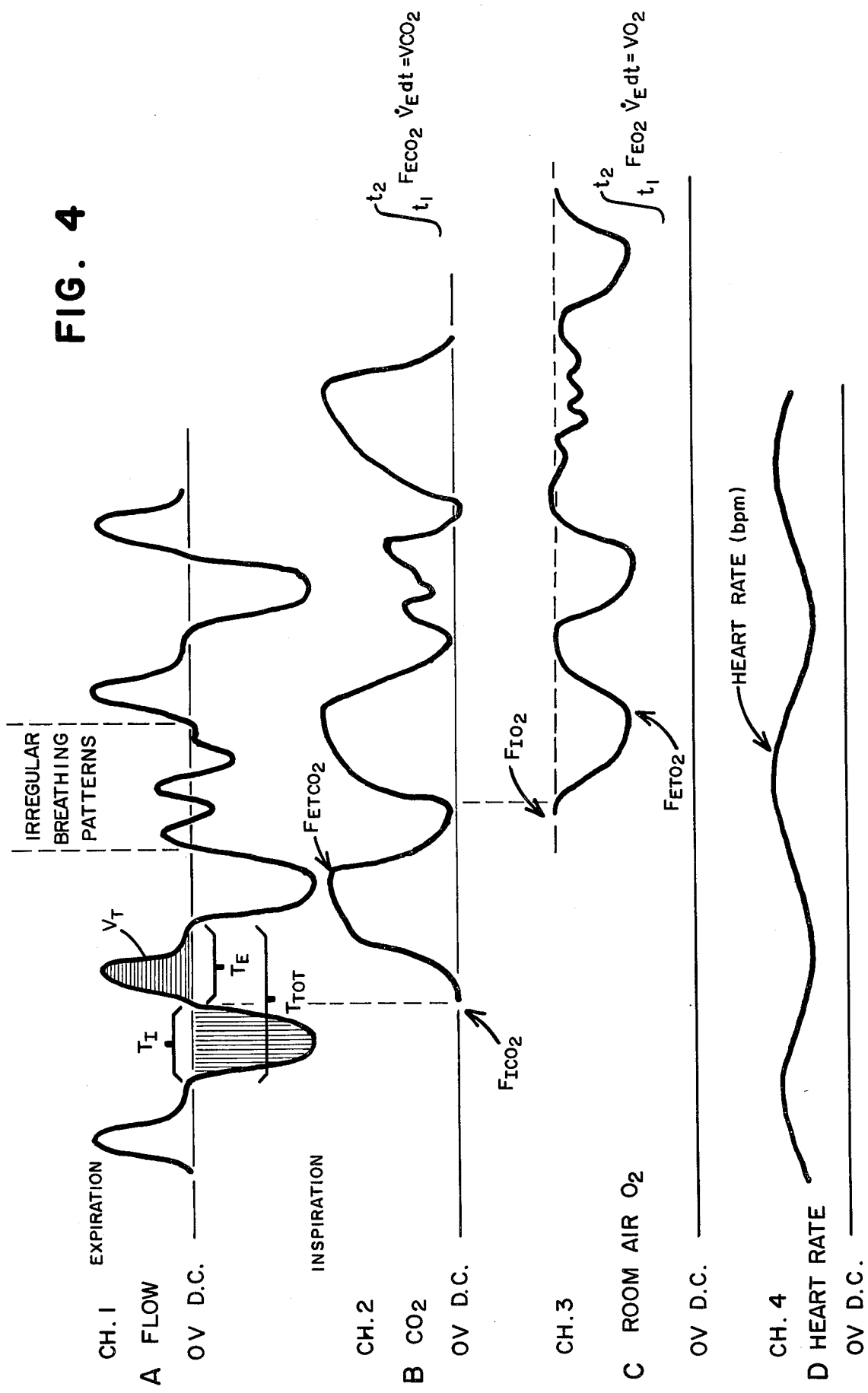
FIG. 4 is illustrative of the analog waveforms applied as inputs to the waveform analyzer of FIG. 2.

With reference to FIG. 4, the signal appearing at the output of the amplifier 70 during any one of the plural sampling periods may be represented by waveform "A" which constitutes the instantaneous flow of the patient's respiratory system measured in milliliters per minute. It is to be noted that for the most part, the flow waveform is quite rhythmical but in the segment bracketed by the vertical dashed lines, the pattern becomes somewhat erratic before again resuming the rhythmical pattern. The erratic portion of the curve may occur during REM sleep which is that sleep associated with rapid eye movements, twitching, etc. or may be caused by a cough or the like. The more rhythmical flow patterns are observed during the patient's deep sleep.

As will be more fully explained, the waveform analyzer 72 operates to eliminate from the various measurements to be plotted any data which would otherwise be based on the erratic portion of the respiratory flow. The waveform analyzer 72 is capable of detecting frequency variations of a received signal from a norm and to create an inhibit condition whereby computations are precluded from taking place on data being obtained until the inhibit situation subsides.

To compute ventilation in milliliters per minute per kilogram of body weight, each breathing cycle of the flow waveform (waveform A of FIG. 4) is effectively divided into its inspiratory time $T_I$, an expiratory time, $T_E$, and pause time or apneic period and by performing integration on the inspiratory amd expiratory flow as represented by the shaded areas of waveform A, one obtains the volume of inspired and expired gas. When each of these volumes is added over a predetermined user selected time interval, the result is the desired ventilation figure. The system of the present invention operates such that data remains current. When a new breath is taken, a frequency counter is incremented and the measured component attributable to the oldest breath which now lies outside of the user selected time interval is dropped off. Then, by dividing the result by the patient's body weight, the desired ventilation parameter $V_E$ is obtained.

The manner in which the analog flow signal is processed to obtain the desired information content therefrom will next be explained. As has already been indicated, waveform A of FIG. 4 is typical of the flow signal obtained from the output of the amplifier 70 in FIG. 2. The inspiratory time $T_I$ comprises the negative half-wave period of a pneumotachograph signal while the total time (TT) is equal to the full wave time of the preceding breath, including the pause time between inspiratory and expiratory phases and is measured in seconds. The tidal volume (TV) is equal to the integrated value of the inspiratory half cycle of the preceding breath and is represented by the shaded areas below the horizontal axis is waveform A. Using these factors, then, the ventilation measured in milliliters per minute and represented by the symbol VE comprises the volume averaged over a user selected time interval and may be expressed by the equation:

$$VE = \frac{(TV_1 + TV_2 + \ldots + TV_n)}{(TT_1 + TT_2 + \ldots + TT_n)} \cdot 60$$

where $(TT_1+TT_2+\ldots+TT_n)$ is greater than or equal to the user selected time interval, $TT_1$ is the oldest time and $TT_n$ is the newest time.

The waveform analyzer functions to eliminate from these computations erratic samples representative of abnormal breathing episodes. Specifically, for any given breath to be considered valid by the system hardware, the tidal volume (TV) or total inspiratory volume for that given breath must exceed a minimum TV established by the operator as a constant. When the total time sums exceed the user selected time interval, then the volume and time for the oldest breath are dropped from computations and the latest volume and time are added in. In this fashion, the data sampled by the waveform analyzer and used for establishing the ventilation factor, VE, is maintained on a current basis.

To obtain the desired $CO_2$ partial pressure, the waveform analyzer operates upon the signal output from the $CO_2$ analyzer 52 by summing the peak value of the impulses (waveform "B") over the same user selected time interval. By integrating the $CO_2$ signal of waveform "B" in FIG. 2, one obtains a value corresponding to the volume of expired $CO_2$ of the patient.

In a similar fashion, the waveform analyzer operates on the $O_2$ signal (waveform "C") by summing the peaks of that wave over the user selected time interval. Then, by integrating this wave, one obtains the volume of expired $O_2$ parameter. The so-called user selected time interval should be such that each of the waves, i.e., flow, $O_2$ and $CO_2$ have the same number of peaks or sampling times per interval.

Upon receipt of an appropriate command signal from the host CPU 84 (FIG. 3) the waveform analyzer will be made to sequentially sample the input channels 1–4 to feed in flow, $CO_2$, $O_2$ and heart rate information. During the transmission and conversion operations, the processor in the waveform analyzer can simultaneously be performing computations on previously received data and, in this fashion, computations and data transmissions may take place in an overlapped fashion. Data flowing from and to the host computer 84 is preferably encoded as a 7 bit ASCII code and transmission rates may be 2400 baud which is compatible with the well-recognized communications protocol of the RS-232C interface specifications.

In that the waveform analyzer utilized in the system of the present invention includes a microprogrammed microprocessor, it is deemed helpful for a complete understanding of the system to set forth, by means of flow charts, a preferred way in which the microprocessor may be programmed to carry out the ventilatory response screening function. Because those skilled in the art will be able to prepare detailed machine coding for the system from the flow chart information provided herein, and because the use of other commercially available microprocessors would dictate alternative machine coding, it is deemed unnecessary to set forth the specific machine coding (microprograms) stored in the microprocessor's RAM And ROM memory modules.

Figure 5A:
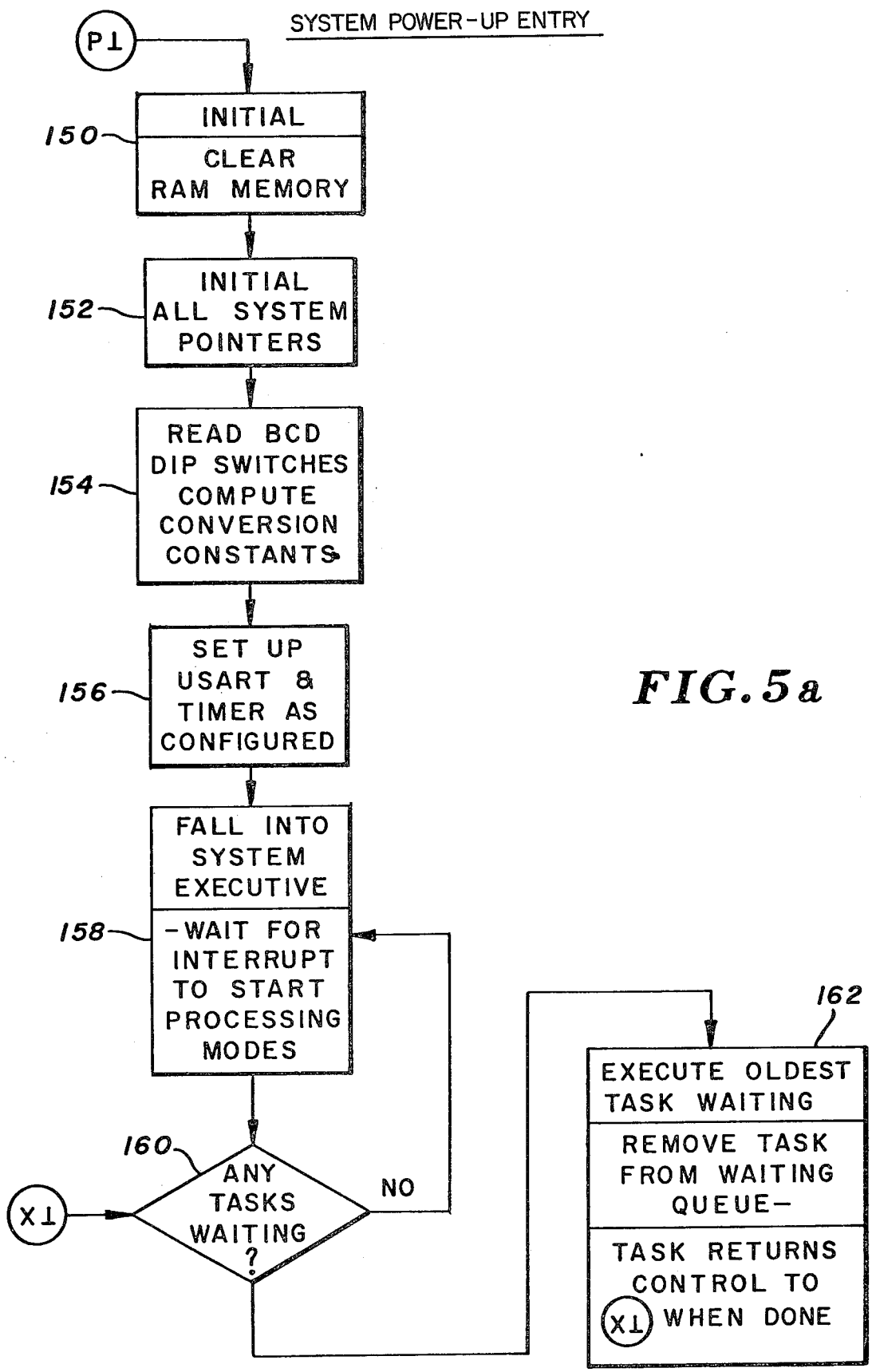

FIG. 5(a) is a flow chart of the operations performed upon system power-up. The microprocessor is interrupt driven following the initialization upon power-up and all tasks are designed to return control to the system executive when they have been completed. Thus, as indicated in FIG. 5(a), upon initialization, the microprocessor's RAM memory is cleared (block 150) and all of the address counters and stack pointers are initialized (block 152). Next, the microprocessor causes certain conversion constants entered manually, such as by suitable switches, or automatically, i.e., under program control to be entered into memory (block 154). The system's communication algorithm, termed USART, is initiated in a manner known to those familiar with the Intel 8085 microprocessor, this operation being represented by block 156 in FIG. 5(a).

The system then enters its executive stream and it waits for the first interrupt to occur whereby one of the various processing modes can be initiated. This operation is represented by block 158 in FIG. 5(a). The decision block 160 provides a means whereby the microprocessor can determine whether any tasks are waiting to be processed. If so, the microprocessor handles them on a first-in, first out basis (block 162). Upon completion of this oldest task, the control returns to entry point X1 and if no other tasks are waiting, the executive sits in an idle mode waiting for the next interrupt to occur.

Figure 5B:
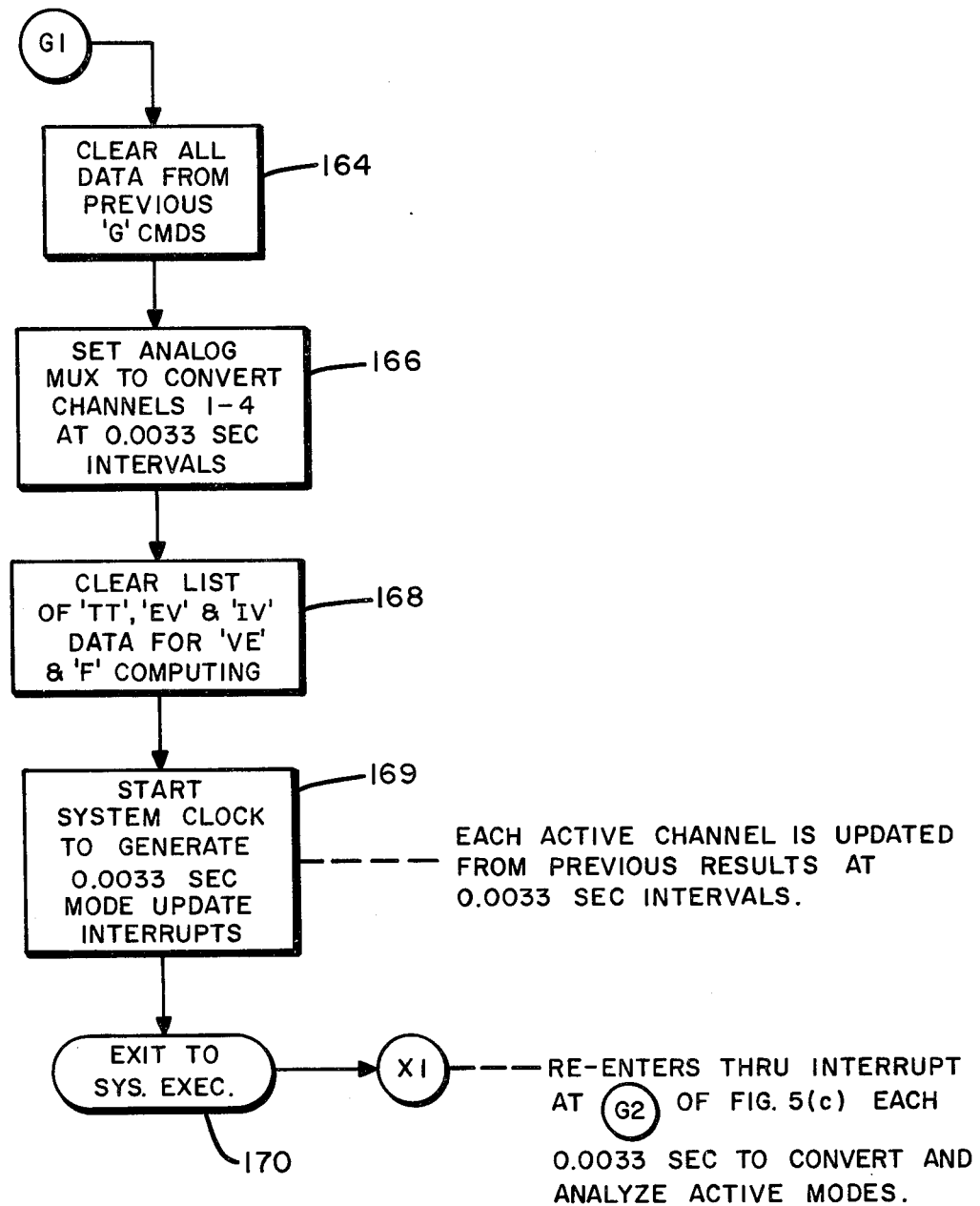

Data from the various sensors 66, 74, 80 and 86 of FIG. 2 are transferred into the waveform analyzer 72 under control of the so-called "G command". The flow chart relating to the "G-Command" is set forth in FIG. 5(b). With reference to this figure, when the waveform analyzer receives the G-Command from the computer, it causes the waveform analyzer's microprocessor to clear all data from a previous command (block 164) and the analog multiplexer 100 of A/D converter of FIG. 3 are set to convert the channels 1–4 at 3.3 millisecond intervals (block 166). Following that, the parameters of total times (TT) expired volume EV and inspired volume, IV, data for computing ventilatory response (VE) and breath frequency (f) from a previous iteration are cleared. This is represented by block 168 in FIG. 5(b). Next, the system clock is initiated such that mode update interrupt signals are outputted at a one millisecond rate and each active channel is up-dated from its previous result at the same 3.3 millisecond intervals. Control is then returned to the system executive at entry point. (X1) (See block 170). The G-Command is re-entered through an interrupt occurring each 3.3 milliseconds, the entry point being at (G2) in the flow chart of FIG. 5(c).

Referring to FIG. 5(c), following entry, the system clock is reset readying it for receipt of a subsequent interrupt. Also, the analog multiplexer 100 and A/D converter 106 are conditioned to begin converting the data received on the active ones of the channels CH.1 through CH.4, these operations being represented by blocks 172 and 174, respectively. As previously described, channel 1 is arranged to receive flow information via the pneumotach and its associated amplifier 70. Channel 2 receives data from the carbon dioxide analyzer while channel 3 is connected to receive data relating to oxygen concentration from the oxygen analyzer 80. Channel 4 is connected to receive heart rate data.

Figures 1, 5D:
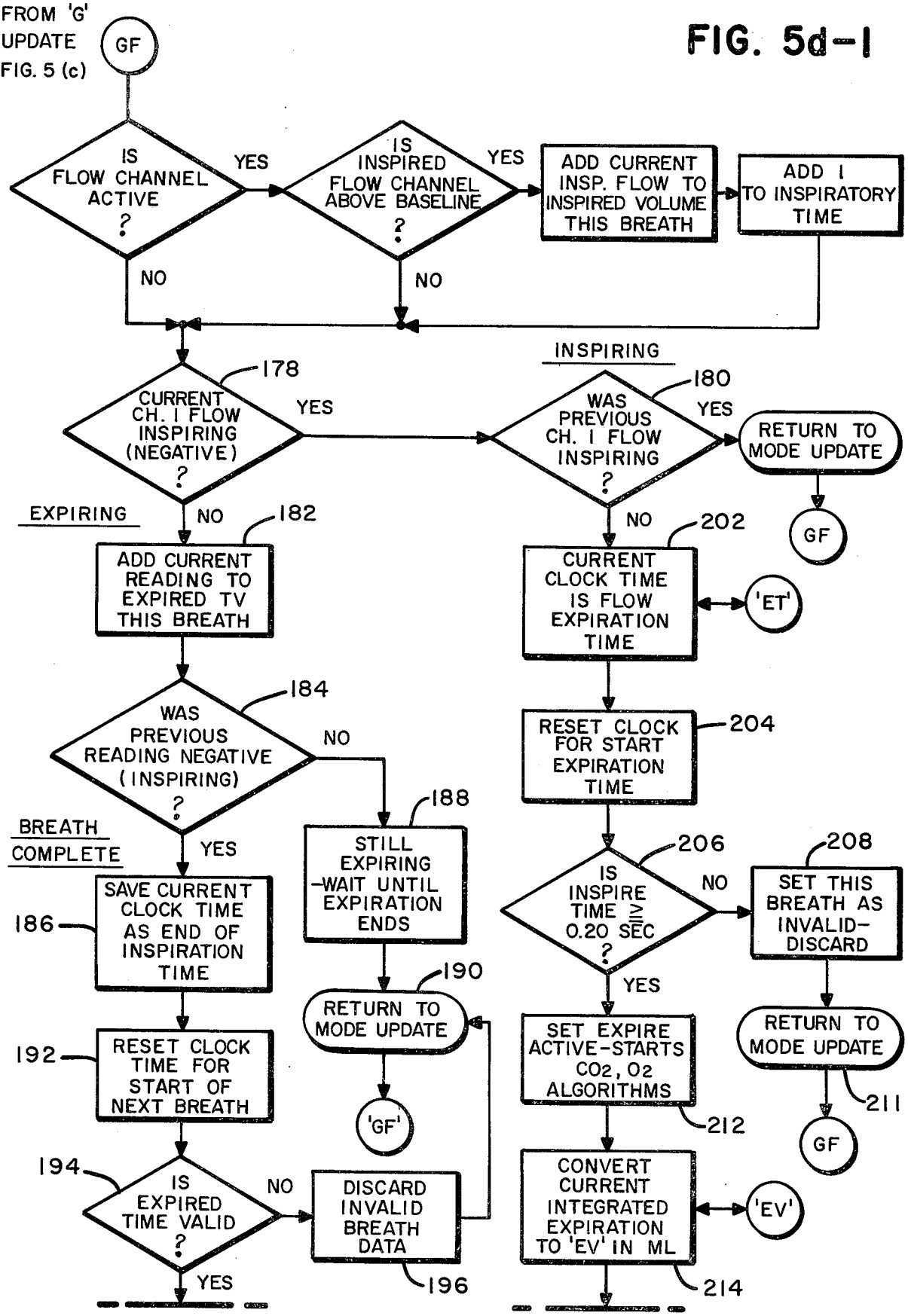
Figures 2, 5D:
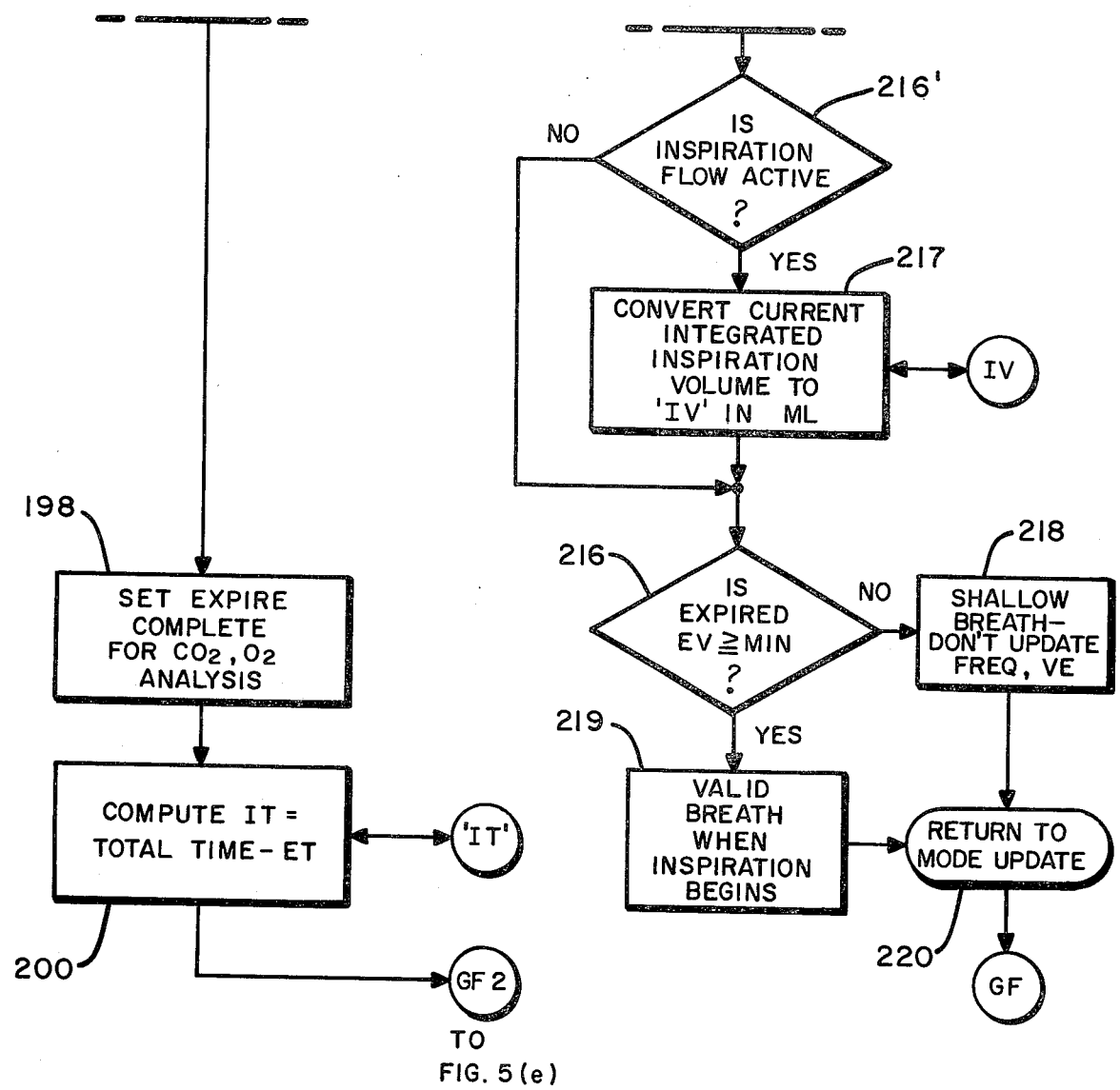
Figure 5E:
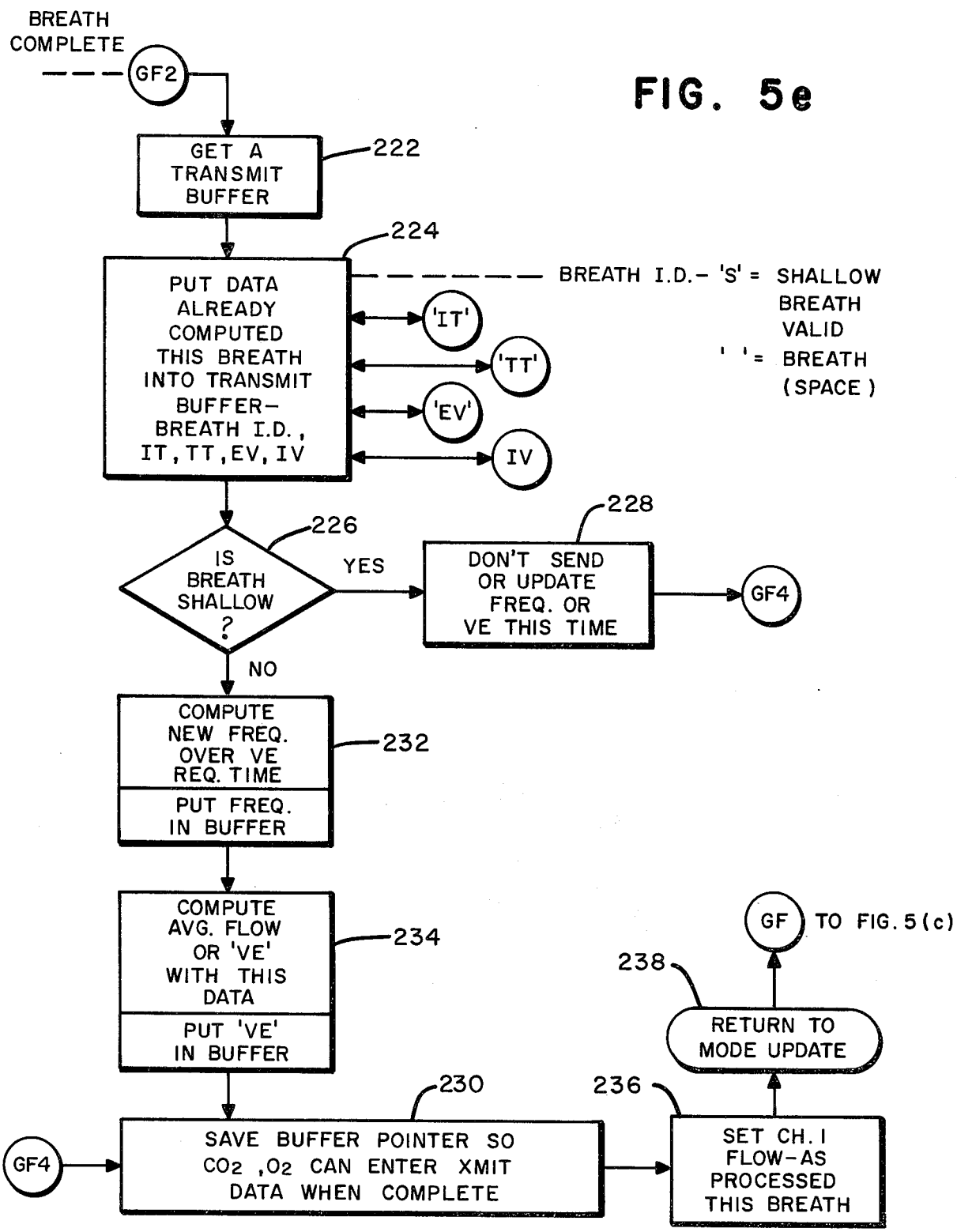

Assuming that channel 1 is active so that the flow information is to be up-dated, as is indicated by the block 176, the software exits to a flow conversion routine which is represented by the flow charts of FIGS. 5(d) and 5(e). Thus, leaving the flow chart of FIG. 5(c) momentarily, consideration will next be given to the operations taking place in the flow conversion process.

As can be seen in FIG. 5(d), control enters at the flag (GF) and at decision block 178′ a determination is made whether the inspired flow channel is active. If not, control returns to the (GF′) flag. However, if the inspired flow channel is active, a test is made to determine if the signal on the inspired flow channel is above the baseline. Again, if not, control exits to the (GF′) flag but if it is above the baseline, the current value of inspired flow is added to the inspired volume of the current breath and the inspiratory time is incremented. At block 178 a determination is made whether the instantaneous data from the pneumotach is representative of the inspiration portion of a complete respiratory cycle. If the waveform is negative, indicating inspiratory flow, the system flows the "Yes" output of block 178 and a determination is made whether the previous sample at channel 1 was indicative of inspiratory flow (block 180). If so, the control is looped back to the entry point (GF) and this sampling process is continued until the sample becomes positive, indicating the onset of an expiratory half-cycle. When this occurs, control exits the "No" path from decision block 178 and, as represented by block 182, the current reading is added to the expired tidal volume (TV) for this breath. Next, at decision block 184, a test is made as to whether the previous reading had been negative. Under our assumed condition, it had been and, hence, the processor's current clock time is stored to later indicate the end of the inspiration time, all as represented by block 186. If the previous reading on channel 1 had still been negative indicative that the inspiration half-cycle had not been completed and the subject was still inspiring, block 188 and 190 comprise a feedback path to the entry point of the decision block 178. Following the output from block 186, then, the flow chart of FIG. 5(d) indicates that clock time is reset to initiate the start time of the next breath.

Next, the expiration time portion of the cycle is compared to a predetermined constant set into the system by manually operated switches on the front panel and if the expiration time is less than the preset time, it is determined to be an invalid breath and the data relating to it is discarded. These operations are represented by the decision blocks 194 and 196, the output of this latter block being again routed so as to reinitiate the flow up-date algorithm by entering at the point (GF). As was indicated earlier, an invalid breath may occur due to an apneic spell or due to coughing or some other respiratory disturbance. The system of the present invention is able to discriminate against such irregular sampling intervals so that it cannot cause erroneous data to be processed.

Assuming that the expired time interval is indicative of a valid breath, a flag indicative that the expiratory cycle has been completed is set, this flag being utilized by the $CO_2$ and $O_2$ analysis routines, all as will be later described. This flag setting operation is represented by block 198. The microprocessor in the waveform analyzer then computes the inspiratory time $T_I$ by subtracting the expiratory time $T_E$ from the total time TT, for that breath (block 200).

The explanation of the flow chart of FIG. 5(d) to this point has assumed that the expiratory cycle was being sampled. At the onset of an inspiration cycle, control exits the "No" path from the decision block 180 and operation 202 is performed whereby the current clock time is recorded as being the end of the expiratory cycle. The manner in which this piece of information is utilized will be described more fully below.

As represented by block 204, the system clock is reset to reflect the start of the expiration time. Again, at decision block 206 a test is made to determine whether the previous inspiratory time was greater than or equal to 0.2 seconds. If not, that breath sample is rejected as invalid and control is returned to the entry point (GF′) of block 178. See blocks 208 and 210 of FIG. 5(d). However, if the test set up in decision block 206 is passed, the "expire active" flag is set and the $CO_2$ and $O_2$ algorithms yet to be described are initiated. This operation is represented by the block 212 in FIG. 5(d).

Next, as is indicated by block 214, the microprocessor in the waveform analyzer functions to integrate the flow curve over the expiratory time interval to generate the expired volume (EV) factor. Next, at decision block 216′ a test is made to determine whether inspiratory flow is "active". If so, the current integrated inspiratory volume is converted to IV in milliliters at operation block 217. Next, at decision block 216 a test is made to determine whether the expired tidal volume is greater than or equal to a preset lower limit tidal volume and, if not, the sample is rejected as invalid (a shallow breath) and the computed value is not used to up-date the frequency and ventilation factors. Instead, control is again returned to the beginning of the "up-date flow" algorithm as represented by the blocks 218 and 220. However, if the expired tidal volume is greater than or equal to the preset lower limit tidal volume, the sampled breath is valid and at the beginning of the inspiratory cycle, control is again returned to the entry point of decision block 178.

Referring next to FIG. 5(e), that flow chart indicates the ensuing operations following the completion of the operation represented by block 200 in FIG. 5(d). Specifically, once a breath sample is complete, a storage buffer is assigned, as represented by block 222, and the data to be transmitted from the waveform analyzer to the computer is assembled in that storage buffer. First, a breath I.D. indicative of a shallow breath or a valid breath is entered into the transmit buffer as is the inspiratory time, the total time, the expired volume and the inspired volume factores, these operations being represented by block 224 in FIG. 5(e). If a shallow breath is involved, the test block 226 routes control such that the assembled data is not sent but, instead, the same buffer area is reserved for later use by the $CO_2$ and $O_2$ sampling routines, this being represented by block 228 and 230 in FIG. 5(e).

Assuming that the breath sample meets established criteria, the decision block 226 will route control such that the next operation, represented by block 232, will take place. That is, a new breath frequency value will be computed by multiplying the number of total time samples (TT) used by sixty (60) and dividing that product by the sum of the total times of breaths obtained in a user selected time interval. Expressed mathematically:

$$F = \frac{60 \times N}{TT_1 + TT_2 + \ldots + TT_n}$$

In the above formula, $TT_1$ is the total time of the oldest breath in the sampling interval and $TT_n$ is the newest or most current total time of a breath sample.

After this computed value is stored in the selected transmit buffer, the next operation for the waveform analyzer microprocessor is to compute ventilation, all as represented by block 234 in FIG. 5(e). This computation has been explained and need not be repeated here. The computed value is also placed in the transmit buffer at a desired location so that once transmitted to the receiving computer, the computer will recognize the data at that location as being related to the ventilation parameter.

Following the operation previously described in connection with block 230, the waveform analyzer sets a flag indicating that the flow up-date operation has been completed and the control may be returned to block 176 in FIG. 5(c). These steps are represented by the blocks labeled 236 and 238 in the flow diagram of FIG. 5(e).

Once control is returned to the "G-Mode Up-date Processor" routine, the next sequential step is represented by the block 240 in FIG. 5(c). This block routes control to the "Up-date $CO_2$" routine set forth in the flow charts of FIGS. 5(f) and 5(g).

Once control passes to the "Up-date $CO_2$" routine, the first step to occur, represented by block 242 in FIG. 5(f), is that a comparison is made between the current amplitude sample of the output from the analyzer 74 to the minimum amplitude from that device for the particular breath in question. If the current reading is less than the previous minimum reading that new reading is stored as the new "minimum" value (block 244). If the test represented by block 246 reveals that the current reading exceeds a previous minimum (or following the storage of the new minimum value) a subsequent test is conducted (represented by decision block 248) and, again, the flow signal on Channel 1 is sampled to determine whether it is negative, indicative that the patient is in the inspiration portion of a breathing cycle. If not inspiring, control is returned to the input point of block 242 as represented by the symbol 250 in FIG. 5(f). This sequencing continues until the test at decision block 248 reveals that the patient has begun an inspiration cycle, and at this point a test is made at 249 to determine whether a predetermined phase lag characteristic of the sampling equipment utilized has expired. If not, the phase delay parameter is decremented by one count. If the phase lag has expired, the current CH.2 reading is multiplied by the equalized phases of the $CO_2$ and flow parameters as represented by block 252. Then, the current $CO_2$ level at channel 2 at the time of sampling is compared to the maximum reading of $CO_2$ level during the expiration cycle of the breath in progress (block 254). Next, the test represented by decision block 256 is carried out whereby a determination is made whether the current $CO_2$ reading comprises a new peak. If so, this current reading is stored as indicative of the peak $CO_2$ value for the breath in question. This operation is represented by block 258 in FIG. 5(f).

Figure 5G:
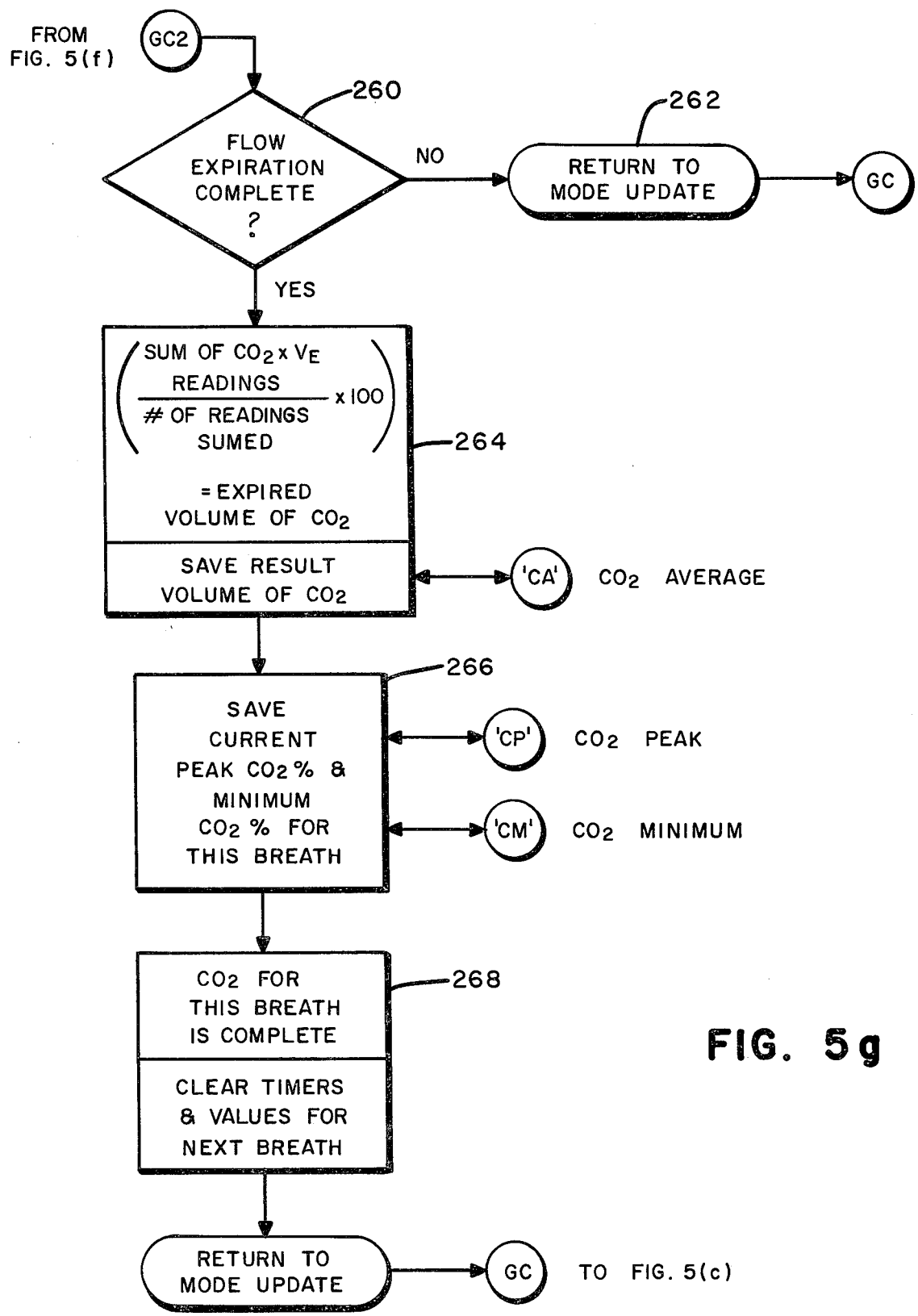

If the current $CO_2$ level does not comprise a new peak or if it does and that peak reading is stored, control is directed to the decision block 260 in FIG. 5(g). Here, a test is made to determine whether the flow expiration has been completed. If not, control is returned to the entry point of the block 242 in FIG. 5(f) as represented by the operation 262. Assuming the expiration cycle is complete, the waveform analyzer's microprocessor is made to compute the expired volume of $CO_2$ of the previous breath during the current inspiratory cycle. The resulting operand is stored and comprises the average expired $CO_2$, thus alleviating the need for a mixing chamber. These operations are identified by block 264 in FIG. 5(g).

If the results of the tests at decision blocks 246 and 256 had been negative such that the minimum $CO_2$ and peak $CO_2$ had not been previously stored, these values are now stored as represented by the block 266. The $CO_2$ parameters for this particular breath have then been completed and the software causes the various timers and previously computed values in the operational registers to be cleared so as to prepare the system for sampling the next succeeding breath. These operations are represented by the block 268 in FIG. 5(g). Control then reverts to the beginning of the "Up-date $CO_2$" sequence at block 242 in FIG. 5(f).

Figure 5I:
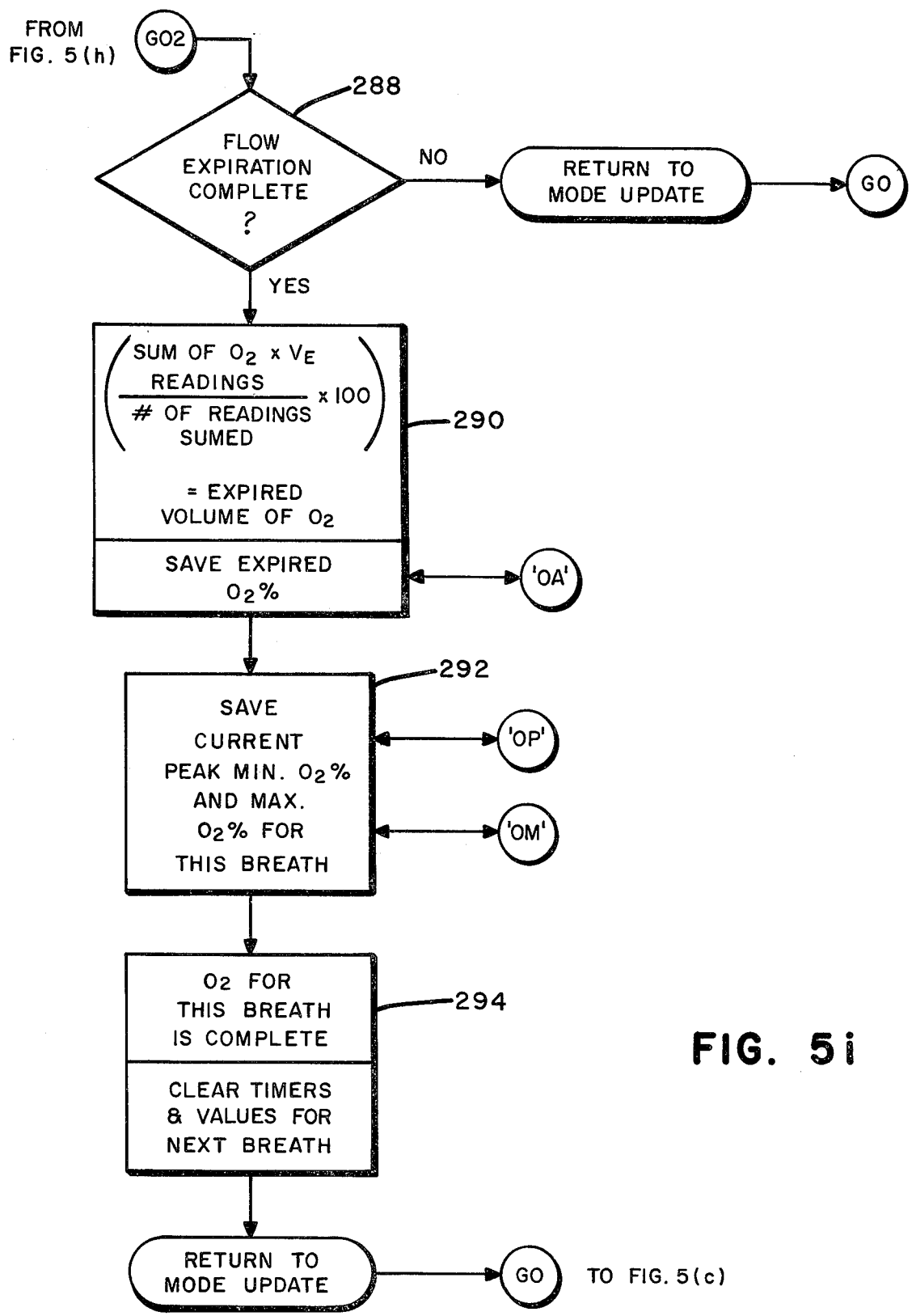

Referring again to the "G-Mode Up-date" algorithm represented by the flow diagram of FIG. 5(c), following completion of the "Up-date $CO_2$" sequence, control reverts to the "Up-date $O_2$" operation represented by block 270. Control exits the block 270 to the sequence represented by the further flow diagrams of FIGS. 5(h) and 5(i). This is the so-called "Up-date $O_2$" sequence and as a first step, represented by block 272, a comparison is made between the instant $O_2$ amplitude on Channel 3 and the maximum reading which had been obtained for this particular breath. At decision block 274, a determination is made as to whether the current sample exceeded any previous sample and, if so, the current reading is stored away as a new maximum $O_2$ value (block 276). Following this operation (or following immediately after the determination is made that the new sample is not a maximum value) the signal on Channel 1 is again sampled to determine whether it is positive, indicative of an expiratory cycle. This test is indicated by decision block 278 in FIG. 5(h) and if the test proves negative, a jump is made back to the original compare step 272. If an expiratory cycle is in progress, a further test is made at 279 to determine whether a predetermined phase delay has elapsed and if not, the phase delay value maintained in a counter is decremented by one count and the operation returns to the compare step 272. If the phase delay has elapsed, the operation represented by block 280 occurs. That is, the current reading on channel 3 (the channel to which the oxygen sensor is connected) is multiplied by equalized phases of $O_2$ and flow. Following that, the current reading taken from the $O_2$ channel is compared to the minimum $O_2$ reading obtained during the expiration time of the current breath (block 282). Block 284 symbolizes the steps to be taken as a result of that comparison. Specifically, if the current channel 3 reading is less than any previous reading taken during that same breath interval, it is considered to be the new minimum peak and that value is stored temporarily as represented by block 286.

Following the storing step, control passes to the flow chart entry point (GO2) on FIG. 5(*i*). As such, in decision block 288 a decision is made whether the expiratory cycle is complete and, if not, the sequence jumps back to the entry point (GO) at block 272 in FIG. 5(*h*). However, if the expiratory flow has been completed, the next step is to compute the expired volume of $O_2$ (FIG. 4C) by summing the products of the expired ventilation $V_E$ and the stored minimum peak $O_2$ readings and dividing the sums by the number of readings involved. The value comprises the expired $O_2$ value expressed as a percent. (See block 290 in FIG. 5(*i*).

Next, if the maximum $O_2$ value and the peak $O_2$ values had not previously been stored as indicated by operations 276 and 286, these values are now stored (block 292) which completes the $O_2$ analysis for this particular breath. At this time, then, the various timers and counters used in the process are cleared or otherwise initiated for repeating the same functions on subsequent breaths. This operation is identified by block 294 in FIG. 5(*i*). Upon completion of that step, control is returned to block 270 in FIG. 5(*c*).

With continued reference to FIG. 5(*c*), if none of the flags (GF), (GC) or (GO) are active, the heart rate HR on channel 4 is next considered. Specifically, a test is made at decision block 296 to determine if only the HR flag is indicating activity. If it is the only active channel requiring up-date, a further test indicated by block 298 is made to determine whether one second has elapsed since a data stream was last transmitted from the waveform analyzer to the computer. If more than one second has elapsed since the previous heart rate data had been sent, the operation symbolized by block 300 is performed such that a new heart rate value in beats/minute is computed and transmitted. Control then returns to the task which had been interrupted to accomplish the foregoing computation and transmission.

If the interrupt had occurred earlier than one second after the preceding heart rate information had been transmitted, a return to the interrupted task takes place immediately without a re-computation and transmission. This is indicated by the operation block 302 in FIG. 5(*c*). Similarly, if the test 296 reveals that other than HR flags are active, a further test is made at 304 to determine whether a breath has been completed. Again, if not, an immediate return to the interrupted task takes place. If, however, the breath had been completed the entire string of data for that particular breath which had previously been formatted is transmitted (block 306) to the receiving computer.

By way of summary, then, it can be seen that the microprocessor in the waveform analyzer under direction of commands sent by the computer 84 is effective to sample, digitize, compute and store in a predetermined message format the data which is useful in evaluating a patient's ventilatory response to changes in $CO_2$ concentrations. While the microprocessor in the waveform analyzer may be programmed to perform still other operations such as calibration, computer diagnostics and data transmission control operations, because these operations are not particularly directed to the generation of the ventilatory response factors, it is deemed unnecessary to describe in detail the flow charts for such routine housekeeping steps. Those knowledgeable in the system architecture and programming of the Intel 8085 Microprocessor will be able to program the system to perform these other functions. As such, it is felt to be unnecessary to set those operations out in any greater detail herein.

FIG. 6 depicts a typical plot obtained from the curve plotter 92 of FIG. 2. As indicated, ventilation, $\dot{V}_E$, measured in milliliters per minute per kilogram of body weight is measured along the ordinate axis while alveolar partial pressure of $CO_2$ is measured along the abscissa. The curve joining the various points plotted tends to be quite linear and to exhibit a significantly higher slope when normal patients are involved. However, the mathematical slope is found to be significantly lower (flatter) in those infants having a propensity towards sleep apnea or SIDS.

Even though heart rate and $O_2$ concentrations are not pertinent to the slope of the curve of FIG. 6, it is essential that the patient's oxygen level be monitored so that it does not drop below approximately 18 percent. This ensures that the response obtained is not a hypoxic response other than the desired response to increased levels of $CO_2$. During the test, the infant may exhibit an apnea attack (extended time period in which no breathing occurs). By monitoring heat rate, it is known that even though normal respiration is not detected, other vital signs are present.

With no limitation intended, one may construct a system in accordance with the present invention by utilizing the following components. It is to be understood, however, that various other devices may be utilized and, accordingly, the devices indicated should not be considered as restricting the invention to any given configuration.

Pneumotach—Fleisch Mo. 0, including a Validyne differential transducer and a Validyne carrier demodulator $CO_2$ analyzer—Model CD102 Aimex $O_2$ analyzer—Model S-3A, Applied Electrochemistry, Inc.

Waveform analyzer 46—Model PF-210, Kiowa Corporation

Computer 60–Tektronix Series 4050

Printer/Plotter—Tektronix Series 4631, Hard Copy Unit

The invention has been described herein in considerable detail, in order to comply with the Patent Statutes and to provide these skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself.

We claim:

1. Apparatus for diagnosing possible brain stem disfunction relating to respiration in a patient comprising:
   (a) means for selectively introducing a plurality of known percentages of a test gas into air being inspired by said patient;
   (b) means for measuring the inspiratory and expiratory flow of air to and from said patient during time periods related to introduction of each such gas percentage and for developing first electrical signals proportional thereto;

(c) means for measuring the percentage concentration of said test gas in the air expired by said patient during time periods related to introduction of each such gas percentage and for producing second electrical signals proportional thereto;

(d) analyzer means, including a programmable computing means, connected to receive said first and second electrical signals for integrating said first signals over respective predetermined time intervals and for computing from said second signals the respective alveolar partial pressure of carbon dioxide gas in the expiratory air flow from the lungs of said patient, said analyzer means further including means for determining the change in said integrated first signals relative to said respective alveolar partial pressures; and (e) display means connected to said analyzer means for displaying said relative change, whereby normal and abnormal ventilatory responses may be distinguished.

2. Apparatus as in claim 1 wherein said means for introducing known percentages of test gas in air being inspired comprises:

(a) means for connecting said source of test gas to the patient's breathing orifices;

(b) sample storage means for storing a plurality of gas samples of known constituent concentrations; and (c) means for selectively connecting said sample storage means to said connecting means.

3. Apparatus as in claim 2 wherein said means for measuring said inspiratory and expiratory flow of air comprises:

(a) a pressure transducing head disposed in said connecting means for sensing differential pressure changes between two predetermined locations therein; and (b) means coupled to said transducing head for converting said differential pressure change into an analog electrical signal comprising said first electrical signals.

4. Apparatus as in claim 3 wherein said analyzer means comprises:

(a) multiplexer means having a plurality of input channels adapted to receive at least said analog electrical signal and said second electrical signal;

(b) analog-to-digital converter means coupled to said multiplexer means for individually receiving signals applied to said plurality of input channels;

(c) said programmable computing means including storage means for holding a program of instructions and operands at addressable locations therein, control means, arithmetic means and input and output means, said input means being coupled to said analog-to-digital converter means for receiving operands therefrom and storing same in said storage means under direction of said control means; and (d) said display means being coupled to said output means of said programmable computing means.

5. Apparatus as in claim 1 wherein said analyzer means further includes means for detecting when inspiratory or expiratory flow patterns fail to meet predetermined criteria.

6. Apparatus as in claim 1 wherein said analyzer means further includes means for detecting intervals during which the integrated value of said first electrical signal one less than a predetermined threshold level; and means responsive to said detecting means for inhibiting said programmable computing means from producing computations based upon said first electrical signal existing during said intervals.

7. A method for diagnosing possible brain stem disfunction relating to respiration in a patient comprising the steps of:

(a) selectively introducing a plurality of known percentages of test gases into air being inspired by said patient;

(b) measuring the inspiratory and expiratory flow of air to and from said patient during time periods related to introduction of each such gas percentage and for developing first electrical signals proportional thereto;

(c) measuring the percentage concentration of carbon dioxide gas in the air expired by said patient during time periods related to introduction of each such gas percentage and for producing second electrical signals proportional thereto;

(d) computing the integral of said first signals over respective predetermined time intervals;

(e) computing from said second signals the respective alveolar partial pressure of carbon dioxide gas in the expiratory air flow from the lungs of said patient;

(f) determining the change in said integrated first signals relative to said respective alveolar partial pressures; and (g) displaying said relative change, whereby normal and abnormal ventilatory responses may be distinguished.

* * * * *

UNITED STATES PATENT AND TRADEMARK OFFICE
CERTIFICATE OF CORRECTION

PATENT NO. : 4,440,177
DATED : April 3, 1984
INVENTOR(S) : Stephen T. Anderson; Catherine A. Anderson It is certified that error appears in the above-identified patent and that said Letters Patent are hereby corrected as shown below:

Column 17, Line 45, "signal" (second occurrence) should read -- signals --.

Column 18, Line 17, "signal one" should read -- signals are --.

Column 18, Line 21, "signal" should read -- signals --.

Signed and Sealed this

Nineteenth Day of June 1984

[SEAL]

Attest:

GERALD J. MOSSINGHOFF

Attesting Officer

Commissioner of Patents and Trademarks